United States Patent [19]

Poulin

[11] Patent Number: 4,774,029

[45] Date of Patent: Sep. 27, 1988

[54] CONDUCTIVE POLYMERS AND METHOD OF PREPARATION THEREOF

[75] Inventor: Albert D. Poulin, New Bedford, Mass.

[73] Assignee: Skeptikos Technology, Inc., Chamblee, Ga.

[21] Appl. No.: 799,246

[22] Filed: Nov. 18, 1985

[51] Int. Cl.⁴ .................. C07C 87/30; H01B 1/00
[52] U.S. Cl. ................... 260/501.15; 252/500
[58] Field of Search ............... 252/500; 260/501.15; 429/212, 213; 136/253; 204/291

[56] References Cited

U.S. PATENT DOCUMENTS

| | | | |
|---|---|---|---|
| 4,077,963 | 3/1978 | Benes et al. ................ | 260/501.15 |
| 4,194,960 | 3/1980 | Bleikamp, Jr. ............... | 204/280 |
| 4,223,243 | 9/1980 | Oliver et al. ................ | 313/268 |
| 4,224,129 | 9/1980 | McIntyre et al. ............. | 204/263 |
| 4,239,661 | 12/1980 | Muraoka et al. ............. | 260/501.15 |
| 4,265,727 | 5/1981 | Beckley ..................... | 204/242 |
| 4,276,110 | 6/1981 | Bilhorn ..................... | 156/298 |
| 4,285,791 | 8/1981 | Schmidt-Rabenau ......... | 204/195 M |
| 4,287,044 | 9/1981 | Biles et al. ................. | 204/231 |
| 4,426,339 | 1/1984 | Kamath et al. .           |            |

OTHER PUBLICATIONS

A Wiley-Interscience Publication, John Wiley & Sons, "Polymers Conductive", Kirk-Othmer Encyclopedia, adbridged version of the 24th vol. Encyclopedia, c1978–c1984.

A Wiley-Interscience Publication, John Wiley & Sons, "Acrylic Acid and Derivatives", Kirk-Othmer Encyclopedia, abridged version of 24th volume, Encyclopedia c1978–c1984.

The Wall Street Journal, "Interest is Growing in Plastics That Can Conduct Electricity", p. 25, Jan. 8, 1982.

Business Week, "Getting a Charge Out of Plastic Batteries", Aug. 17, 1987.

High Technology, "Chemistry's New Workhorse", Jul. 1987.

Albert D. Poulin, "Liquid Salts as Inverse Micellular Structures", prepared for Oral Examination, May 30, 1977.

*Primary Examiner*—Josephine Barr
*Attorney, Agent, or Firm*—Jones, Askew & Lunsford

[57] ABSTRACT

The present invention relates to a compound that can be reacted with a polymer resin to form the conductive polymer. More particularly, the present invention relates to a tetraalkylammonium acrylate that can be reacted with a conventional acrylic resin to form a stable, conductive polymer that will conduct electricity but is impermeable to liquids.

The tetraalkylammonium acrylate has the following general structure:

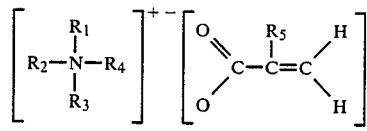

wherein:

$R_1$, $R_2$, $R_3$, and $R_4$ are alkyl groups of from 3 to 18 carbon atoms; and $R_5$ is a hydrogen or an alkyl group of from 1 to 3 carbon atoms.

The conductive polymer of the present invention is suitable for use as the electricity conducting barrier in reference electrodes.

3 Claims, 1 Drawing Sheet

CONDUCTIVE POLYMERS AND METHOD OF PREPARATION THEREOF

TECHNICAL FIELD

The present invention relates to a compound capable of conducting electricity. More particularly, the present invention relates to a tetraalkylammonium acrylate which can be reacted with a conventional acrylic resin to form a stable, conductive polymer with such properties as a range of flexibilities and impermeability to liquids such as water.

BACKGROUND ART

Useful organic polymers, such as polyethylenes, polyesters and polymethacrylates are not capable of intrinsically conducting electricity. Electrical conductivity in these instances is achieved by either coating the polymer with an intrinsically conductive material, e.g. a metal film or powdered graphite, or by incorporating a powdered metal or grahite as an admixture or composite, e.g. suspending a sufficient quantity of powdered graphite in the monomer vehicle prior to polymerization. In these instances, the conductivity depends on the mechanical connections of contiguous, conductive particles in numerous pathways or in the continuity of a conductive film. In these types of admixtures, the electricity is conveyed by movement of electrons in or on the surface of the conductive particles or films, and not in the polymer.

Later, synthetic compounds were developed which mimicked the molecular orbital structures of graphite materials. An example of such a polymer is the polytetracyanoethylenes. Conduction in these graphitic-like structures depends on electron movement through the overlapping "pi" molecular orbitals. In all of these synthetic compounds which mimic the molecular orbital structures of the graphitic materials, electrical conduction is by electron movement within the material.

The polymer of the present invention entails a polymer that does not conduct electricity by means of electron movement, but by ion transport as opposed to the polymers of the prior art.

SUMMARY OF THE INVENTION

The present invention provides an intrinsically ionically conductive compound. The present invention also provides an electrically conductive polymer prepared by polymerizing the electrically conductive compound with a suitable acrylic resin. The polymer is prepared from an intrinsically conductive liquid salt and suitable comonomer system. The present invention is highly resistant to aqueous solutions and a variety of chemicals. The conductive polymer provides a conductive polymer that can be cast into a variety of shapes and is highly durable and resistant to mechanical shocks. The conductive properties of the conductive polymer of the present invention do not appreciably change over time.

An important attribute of the electrically conductive compound and polymer of the present invention is that electrical conduction arises from ionic movement whereas in the electrically conductive compounds of the prior art, the electrical conductivity arises from electron movement.

The electrically conductive compound of the present invention comprises a tetraalkylammonium acrylate.

The tetraalkylammonium acrylate useful in the present invention has the following general structure:

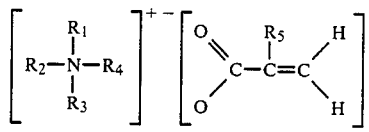

wherein:
R$_1$, R$_2$, R$_3$, and R$_4$ are alkyl groups of from 3 to 18 carbon atoms; and
R$_5$ is a hydrogen or an alkyl group of from 1 to 3 carbon atoms.

The electrically conductive polymer of the present invention is prepared by polymerizing the tetraalkylammonium acrylate of the present invention with a suitable polymer resin, such as an acrylic resin.

The conductive polymer of the present invention can be used under chemically harsh conditions. The polymer of the present invention is highly resistant to both acidic and basic aqueous solutions and is resistant to most commonly used solvents.

The conductive polymer of the present invention can be used, for example, as an impermeable conductive salt bridge between a sample solution and the internal solution of a reference electrode.

Reference electrodes for electrochemical measurements of the prior art have always used some permeability to establish conductivity between the reference electrode solution and the sample solution. For continuous, long-term measurements, this permeability is unacceptable sinc mechanical blockage may occur, or worse, the sample solution slowly permeates into the reference electrode solution causing the half-cell potential of the reference electrode to change in an unknown manner. A reference electrode constructed with the polymer of the present invention as the barrier is impermeable to liquids; therefore, the reference electrode solution cannot become contaminated. The barrier of the reference electrode can have a large surface area since the polymer of the present invention is castable thereby minimizing mechanical surface blockage. Indeed, such a reference electrode can be made as a flow-through electrode.

The conductive polymer of the present invention can also be used as a coating where it is necessary to carry off static electricity. For example, the conductive polymer can be used to coat the tank of a gasoline truck. When static electricity builds up due to the sloshing of the fluid in the truck, the conductive polymer allows the static electricity to be safely conducted to ground.

Accordingly, it is an object of the present invention to provide an improved electrically conductive compound and polymer.

Another object of the present invention is to provide a conductive polymer formed by polymerizing conductive tetraalkylammonium acrylate.

Yet another object of the present invention is to provide a conductive polymer that is fluid impermeable.

Another object of the present invention is to provide a conductive polymer that is resistant to mechanical shock.

Another object of the present invention is to provide a conductive polymer as a pressure transducer whereby mechanical distortion will change the electrical resistance due to changes in cross-sectional area.

Yet another object of the present invention is to provide a conductive polymer that is stable to hostile environments.

Another object of the present invention is to provide a conductive polymer for use as a solid electrolyte in a voltage reference battery.

Another object of the present invention is to provide a conductive polymer wherein said polymer can be incorporated as the reference solution in a reference electrode while also being the barrier.

Another object of the present invention is to provide a conductive polymer for production of printed circuits by either screen-painting or off-set printing the conductive polymer during polymerization thereof.

Another object of the present invention is to provide a conductive polymer as an interface between terminals of electronic devices and biological systems.

Other objects, features and advantages of the present invention will become apparent upon reading the following specification when taken in conjunction with the claims.

DETAILED DESCRIPTION OF THE PREFERRED EMBODIMENT

Figure 1:
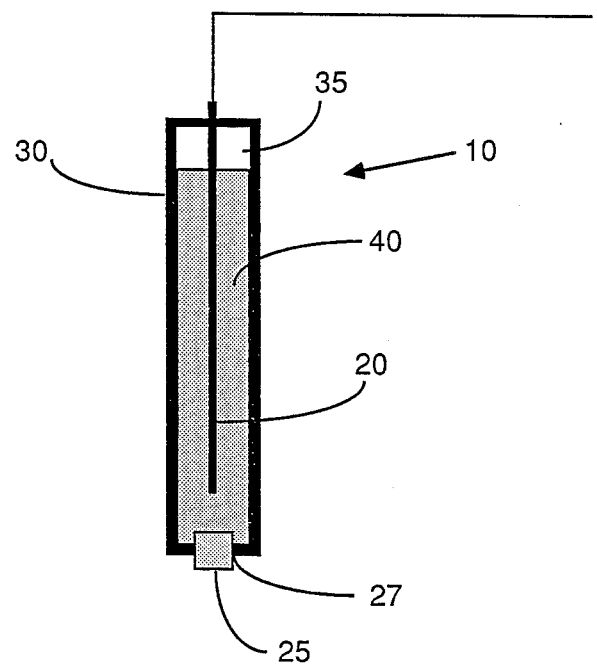
FIG. 1 is a cross-sectional view of an electrode using a disclosed embodiment of the conductive polymer of the present invention as a barrier between the reference electrolyte and the surrounding fluid.

The present invention comprises an electrically conductive compound which can also be polymerized with an acrylic resin. The electrically conductive compound in accordance with the present invention is a novel tetraalkylammonium acrylate compound. The conductive tetraalkylammonium acrylate, when mixed with an acrylic resin, thereby forms a conductive polymer. The polymer can be made soft or hard. It can be formed into a variety of shapes including, but not limited to, cylinders for use in electrodes.

The tetraalkylammonium acrylate compound in accordance with the present invention has the following general structure:

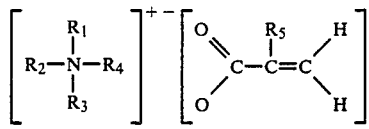

wherein:

$R_1$, $R_2$, $R_3$, and $R_4$ are alkyl groups of from 3 to 18 carbon atoms; and $R_5$ is a hydrogen or an alkyl group of from 1 to 3 carbon atoms.

A preferred structure of the conductive tetraalkylammonium acrylate compound has the following formula:

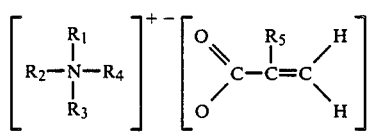

wherein:

$R_1$, $R_2$, $R_3$, and $R_4$ are alkyl groups of from 4 to 8 carbon atoms; and $R_5$ is a hydrogen or an alkyl group of from 1 to 3 carbon atoms.

The most preferred structure of the conductive tetraalkylammonium acrylate compound has the following formula:

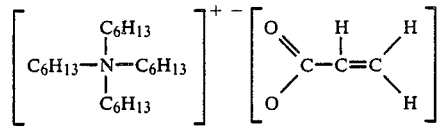

The conductive polymer of the present invention is formed by reacting the tetraalkylammonium acrylate in accordance with the present invention with an acrylic resin, such as unsaturated o-phthalate polyester styrene. The cross-linking reaction is started with a suitable catalyst such as methyl ethyl ketone peroxide.

Tetraalkylammonium acrylates in accordance with the present invention are prepared by reacting tetraalkylammonium iodide with an aqueous solution of silver hydroxide. The silver hydroxide should be freshly prepared for optimum results. The product of the reaction is tetraalkylammonium hydroxide. The tetraalkylammonium hydroxide compound is then partially neutralized with acrylic acid. Another acrylate that can be used in preparing the conductive polymer of the present invention, includes but is not limited to, methacrylate.

The conductive polymer is prepared by polymerizing the tetraalkylammonium acrylate with a suitable acrylic resin. It is to be understood that commercially available tetraalkylammonium hydroxide can be used to prepare the conductive compound of the present invention.

Various acrylic resins can be used in the preparations of the electrically conductive polymer of the present invention. A representative acrylic resin that is suitable for use in the present invention is Castolite ™ "FC" brand (Castolite Co., Woodstock, Ill.) which is an unsaturated o-phthalate polyester styrene. To form the polymer, equal volumes of the acrylic resin and the tetraalkylammonium acrylate are mixed together. A small amount of a catalyst such as methyl ethyl ketone peroxide is then added to the mixture and the polymer is allowed to form.

FIG. 1 is a cross-sectional view of an electrode 10 with a disclosed embodiment of the conductive polymer of the present invention as the conductive barrier between a reference buffer and a sample solution. The electrode 10 includes a chamber 35 containing a solution of sodium sulfide 40. The chamber 40 is constructed of a nonconducting material, such as acrylic or other suitable material. The chamber 35 defines an opening 27 through which is positioned a plug 25 of the conductive polymer of the present invention. The conductive polymer plug 25 is sealed around the edges of opening 27 so that the surrounding external fluid cannot enter the chamber 35. Extending into the chamber 35 is an internal reference electrode 20 comprising a silver wire. It will be understood by those of ordinary skill in the art that the electrode functions may be changed by changing the composition of the electrolyte solution in chamber 35.

The conductive polymer of the present invention can also be used as a coating for use as a conductive covering on a surface. For example, the conductive polymer of the present invention can be used to coat the inside of a gasoline container on a tank truck. As the tank truck is moving, any static electricity that builds up due to the movement of gasoline in the tank is harmlessly grounded through the conductive polymer.

The conductive polymer of the present invention can be used as a solid electrolyte in a voltage reference battery. If the leads of two separate wires of dissimilar metal, e.g. silver and copper are immersed during polymerization of the polymer of the present invention, a reference voltage source is developed.

The conductive polymer of the present invention can also be used as the conductive pathway in a printed circuit board. The prepolymerized tetraalkylammonium acrylate is scree-paint of off-set printed onto a support board. The tetralkylammonium acrylate is then allowed to polymerize on the support board thereby providing an electrically conductive pathway on the support board.

The following examples of the present invention are provided by way of illustration and are not intended to limit the scope thereof.

EXAMPLE I

To prepare 0.1 moles of tetrahexylammonium acrylate, 0.5 moles of AgOH (Aldrich Chemical Co., Milwaukee, WI) are prepared from 0.5 moles of $AgNO_3$. The $AgNO_3$ is dissolved in 400 ml of water. Separately, 20 g of sodium hydroxide, NaOH, are dissolved in 100 ml of water. The NaOH solution is mixed with the $AgNO_3$ solution whereupon a very dark brown precipitate of AgOH results. The reaction is nearly instantaneous. After thorough mixing, the AgOH is allowed to settle The supernatant containing excess NaOH and by-product sodium nitrate is decanted and discarded. The decantation is repeated until the pH is nearly 7 and constant as determined by pH test papers. Four decantations are usually sufficient. Next, the water is displaced. This is accomplished by at least four repeated decantations using water-free methanol, $CH_3OH$. The methanol decantations and the reaction of AgOH with tetraalkylammonium iodide solution should be performed within 8 hours of the AgOH synthesis.

The AgOH is resuspended in 400 ml of methanol. The purified tetraalkylammonium iodide (0.1 moles or 48.2 g) (Aldrich Chemical Co., Milwaukee, WI) is dissolved separately in 100 ml. of methanol and added to the AgOH suspension. Almost immediately, the AgOH develops a greenish cast. The mixture is stirred for an hour and then filtered through a sintered-glass funnel. The filtrate now contains 0.1 moles of tetrahexylammonium hydroxide. A small amount of phenolphthalein is added, turning the solution red indicating that the solution is basic. Acrylic acid is added until the red color disappears. The methanol is removed by evaporation in a rotary flash evaporator leaving tetrahexylammonium acrylate. The resulting tetrahexylammonium acrylate was found to be electrically conductive.

EXAMPLE II

To prepare 0.1 moles of tetraheptylammonium acrylate, 0.5 moles of AgOH are prepared from 0.5 moles of $AgNO_3$. The $AgNO_3$ is dissolved in 400 ml of water. Separately, 20 g of sodium hydroxide, NaOH, are dissolved in 100 ml of water. The NaOH solution is mixed with the $AgNO_3$ solution whereupon a very dark brown precipitate of AgOH results. The reaction is nearly instantaneous. After thorough mixing, the AgOH is allowed to settle The supernatant containing excess NaOH and by-product sodium nitrate is decanted and discarded. The decantation is repeated until the pH is nearly 7 and constant as determined by pH test papers. Four decantations are usually sufficient. Next, the water is displaced. This is accomplished by at least four repeated decantations using water-free methanol, $CH_3OH$. The methanol decantations and the reaction of AgOH with tetraalkylammonium iodide solution should be performed within 8 hours of the AgOH synthesis.

The AgOH is resuspended in 400 ml of methanol. Purified tetraalkylammonium iodide (0.1 moles or 53.77 g) (Aldrich Chemical Co., Milwaukee, WI) is dissolved separately in 100 ml. of methanol and is added to the AgOH suspension. Almost immediately, the AgOH develops a greenish cast. The mixture is stirred for an hour and then filtered through a sintered-glass funnel. The filtrate now contains 0.1 moles of tetraheptylammonium hydroxide. A small amount of phenolphthalein is added, turning the solution red indicating that the solution is basic. Acrylic acid is added until the red color disappears. The methanol is removed by evaporation in a rotary flash evaporator leaving tetraheptylammonium acrylate. The resulting tetraheptylammonium acrylate was found to be electrically conductive.

EXAMPLE III

To prepare tetrabutylammonium acrylate, a small amount of phenophthalein is added to 0.1 moles of tetrabutylammonium hydroxide (Aldrich Chemical Co., Milwaukee, WI) turning the solution red indicating that the solution is basic. Acrylic acid is added until the red color disappears. The methanol is removed by evaporation in a rotary flash evaporator leaving tetrabutylammonium acrylate. The resulting tetrabutylammonium acrylate was found to be electrically conductive.

EXAMPLE IV

The alkylammonium acrylate polymer is prepared by thoroughly mixing 3 ml of the alkylammonium acrylate monomer from Example I, Example II, or Example III and 3 ml of the acrylic resin Castolite TM . 0.1 ml of the catalyst methyl ethyl ketone peroxide is then added to the solution and the polymer is allowed to form as is well known to one of ordinary skill in the art. The resulting polymers prepared from Examples I, II and III were found to be electrically conductive.

EXAMPLE V

A tetraalkylammonium methacrylate is prepared by substituting methacrylic acid for the acrylic acid in Example I, Example II, and Example III. All of these compounds were found to be electrically conductive.

It should be understood, of course, that the foregoing relates only to a preferred embodiment of the present invention and that numerous modifications or alterations may be made therein without departing from the spirit and the scope of the invention as set forth in the appended claims.

I claim:

1. A electrically conductive compound comprising a tetraalkylammonium acrylate, said tetraalkylammonium acrylate having the following formula:

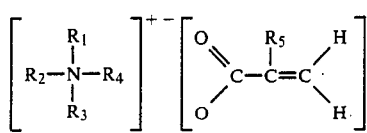

wherein:

R$_1$, R$_2$, R$_3$, and R$_4$ are alkyl groups of from 3 to 18 carbon atoms; and R$_5$ is a hydrogen or an alkyl group of from 1 to 3 carbon atoms.

2. The electrically conductive compound of claim 1 wherein said tetraalkylammonium acrylate has the following formula:

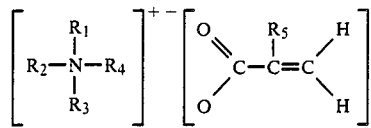

wherein:

R$_1$, R$_2$, R$_3$, and R$_4$ are alkyl groups of from 4 to 8 carbon atoms; and R$_5$ is a hydrogen or an alkyl group of from 1 to 3 carbon atoms.

3. The electrically conductive compound of claim 1 wherein said tetraalkylammonium acrylate has the following formula:

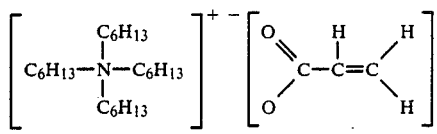

* * * * *